United States Patent [19]
Campbell et al.

[11] Patent Number: 5,771,712
[45] Date of Patent: Jun. 30, 1998

[54] HYDROCARBON GAS PROCESSING

[75] Inventors: Roy E. Campbell; John D. Wilkinson; Hank M. Hudson, all of Midland, Tex.

[73] Assignee: Elcor Corporation, Dallas, Tex.

[21] Appl. No.: 696,114

[22] Filed: Aug. 13, 1996

Related U.S. Application Data

[63] Continuation of Ser. No. 477,423, Jun. 7, 1995, abandoned.
[51] Int. Cl.[6] ........................................................ F25J 3/02
[52] U.S. Cl. ................................................ 62/621; 62/625
[58] Field of Search ...................................... 62/621, 625

[56] References Cited

U.S. PATENT DOCUMENTS

| | | | |
|---|---|---|---|
| Re. 33,408 | 10/1990 | Khan et al. ................................. | 62/29 |
| 4,157,904 | 6/1979 | Campbell et al. .......................... | 62/27 |
| 4,171,964 | 10/1979 | Campbell et al. .......................... | 62/24 |
| 4,251,249 | 2/1981 | Gulsby ....................................... | 62/28 |
| 4,278,457 | 7/1981 | Campbell et al. .......................... | 62/24 |
| 4,519,824 | 5/1985 | Huebel ....................................... | 62/26 |
| 4,617,039 | 10/1986 | Buck .......................................... | 62/26 |
| 4,687,499 | 8/1987 | Aghill ......................................... | 62/24 |
| 4,689,063 | 8/1987 | Paradowski et al. . | |
| 4,690,702 | 9/1987 | Paradowski et al. . | |
| 4,710,214 | 12/1987 | Sharma et al. ............................. | 62/621 |
| 4,718,927 | 1/1988 | Bauer et al. ................................ | 62/621 |
| 4,851,020 | 7/1989 | Montgomery, IV ....................... | 62/621 |
| 4,854,955 | 8/1989 | Campbell et al. .......................... | 62/24 |
| 4,869,740 | 9/1989 | Campbell et al. .......................... | 62/24 |
| 4,889,545 | 12/1989 | Campbell et al. .......................... | 62/24 |
| 4,895,584 | 1/1990 | Buck et al. ................................. | 62/621 |
| 5,275,005 | 1/1994 | Campbell et al. .......................... | 62/621 |

*Primary Examiner*—Ronald C. Capossela
*Attorney, Agent, or Firm*—Baker & Botts, L.L.P.

[57] ABSTRACT

A process for the recovery of propane, propylene and heavier hydrocarbon components from a hydrocarbon gas stream is disclosed. The stream is cooled and/or expanded to partially condense it, then separated to provide a first vapor stream. The first vapor stream is directed into a contacting device whereby a third vapor stream and a $C_3$-containing liquid stream are formed. The $C_3$-containing liquid stream is directed to a distillation column wherein a second vapor stream is separated to recover a product containing the major portion of the $C_3$ components and heavier hydrocarbon components. The second vapor stream is directed into heat exchange relation with the third vapor stream to cool the second vapor stream and condense at least a part of it, forming a condensed stream. At least a portion of the condensed stream is directed to the contacting device to intimately contact the first vapor stream; the remaining portion of the condensed stream is supplied to the distillation column as its top feed. The quantities and temperatures of the feeds to the contacting device and the distillation column are effective to maintain the overhead temperatures of the contacting device and the distillation column at temperatures whereby the major portion of the desired components is recovered.

10 Claims, 6 Drawing Sheets

HYDROCARBON GAS PROCESSING

This application is a continuation of application Ser. No. 08/477,423, filed on Jun. 7, 1995 now abandoned.

BACKGROUND OF THE INVENTION

This invention relates to a process for the separation of a gas containing hydrocarbons.

Propane and heavier hydrocarbons can be recovered from a variety of gases, such as natural gas, refinery gas, and synthetic gas streams obtained from other hydrocarbon materials such as coal, crude oil, naphtha, oil shale, tar sands, and lignite. Natural gas usually has a major proportion of methane and ethane, i.e., methane and ethane together comprise at least 50 mole percent of the gas. The gas also contains relatively lesser amounts of heavier hydrocarbons such as propane, butanes, pentanes and the like, as well as hydrogen, nitrogen, carbon dioxide and other gases.

The present invention is generally concerned with the recovery of propylene, propane and heavier hydrocarbons from such gas streams. A typical analysis of a gas stream to be processed in accordance with this invention would be, in approximate mole percent, 92.6% methane, 4.7% ethane and other $C_2$ components, 1.0% propane and other $C_3$ components, 0.2% iso-butane, 0.2% normal butane, 0.16% pentanes plus, with the balance made up of nitrogen and carbon dioxide. Sulfur containing gases are also sometimes present.

The historically cyclic fluctuations in the prices of both natural gas and its natural gas liquid (NGL) constituents have reduced the incremental value of propane and heavier components as liquid products. This has resulted in a demand for processes that can provide more efficient recoveries of these products. Available processes for separating these materials include those based upon cooling and refrigeration of gas, oil absorption, and refrigerated oil absorption. Additionally, cryogenic processes have become popular because of the availability of economical equipment that produces power while simultaneously expanding and extracting heat from the gas being processed. Depending upon the pressure of the gas source, the richness (ethane and heavier hydrocarbons content) of the gas, and the desired end products, each of these processes or a combination thereof may be employed.

The cryogenic expansion process is now generally preferred for propane recovery because it provides maximum simplicity with ease of start up, operating flexibility, good efficiency, safety, and good reliability. U.S. Pat. Nos. 4,157,904, 4,171,964, 4,251,249, 4,278,457, 4,519,824, 4,617,039, 4,687,499, 4,854,955, 4,869,740, and 4,889,545, reissue U.S. Pat. No. 33,408 and co-pending application Ser. No. 08/337,172 describe relevant processes.

In a typical cryogenic expansion recovery process, a feed gas stream under pressure is cooled by heat exchange with other streams of the process and/or external sources of refrigeration such as a propane compression-refrigeration system. As the gas is cooled, liquids may be condensed and collected in one or more separators as high-pressure liquids containing some of the desired $C_3$+ components. Depending on the richness of the gas and the amount of liquids formed, the high-pressure liquids may be expanded to a lower pressure and fractionated. The vaporization occurring during expansion of the liquids results in further cooling of the stream. Under some conditions, pre-cooling the high pressure liquids prior to the expansion may be desirable in order to further lower the temperature resulting from the expansion. The expanded stream, comprising a mixture of liquid and vapor, is fractionated in a distillation (deethanizer) column. In the column, the expansion cooled stream(s) is (are) distilled to separate residual methane, ethane, nitrogen, and other volatile gases as overhead vapor from the desired $C_3$ components and heavier hydrocarbon components as bottom liquid product.

If the feed gas is not totally condensed (typically it is not), the vapor remaining from the partial condensation can be passed through a work expansion machine or engine, or an expansion valve, to a lower pressure at which additional liquids are condensed as a result of further cooling of the stream. The pressure after expansion is slightly below the pressure at which the distillation column is operated. The expanded stream then enters the lower section of an absorption column and is contacted with cold liquids to absorb the $C_3$ components and heavier components from the vapor portion of the expanded stream. The liquids from the absorption column are then pumped into the deethanizer column at an upper column feed position.

The overhead distillation stream from the deethanizer passes in heat exchange relation with the residue gas from the absorber column and is cooled, condensing at least a portion of the distillation stream from the deethanizer. The cooled distillation stream then enters the upper section of the absorption column where the cold liquids contained in the stream can contact the vapor portion of the expanded stream as described earlier. Typically, the vapor portion (if any) of the cooled distillation stream and the absorber overhead vapor combine in an upper separator section in the absorber column as residual methane and ethane product gas. Alternatively, the cooled distillation stream may be supplied to a separator to provide vapor and liquid streams. The vapor is combined with the absorber column overhead and the liquid is supplied to the absorber column as a top column feed.

The separation that takes place in this process (producing a residue gas leaving the process which contains substantially all of the methane and $C_2$ components in the feed gas with essentially none of the $C_3$ components and heavier hydrocarbon components, and a bottoms fraction leaving the deethanizer which contains substantially all of the $C_3$ components and heavier hydrocarbon components with essentially no methane, $C_2$ components or more volatile components) consumes energy for feed gas cooling, for reboiling the deethanizer, for refluxing the deethanizer, and/or for re-compressing the residue gas. The present invention provides a means for achieving this separation while substantially reducing the utility requirements (cooling, reboiling, refluxing, and/or re-compressing) needed for the recovery of the desired products.

In accordance with the present invention, it has been found that $C_3$ recoveries in excess of 93 percent can be maintained while providing essentially complete rejection of $C_2$ components to the residue gas stream. In addition, the present invention makes possible essentially 100 percent separation of $C_2$ components and lighter components from the $C_3$ components and heavier hydrocarbon components at reduced energy requirements. The present invention, although applicable at lower pressures and warmer temperatures, is particularly advantageous when processing feed gases in the range of 400 to 800 psia or higher under conditions requiring column overhead temperatures of $-50°$ F. or colder.

For a better understanding of the present invention, reference is made to the following examples and drawings. Referring to the drawings:

FIG. 1 is a flow diagram of a prior art cryogenic natural gas processing plant;

FIG. 2 is a flow diagram of a cryogenic expansion natural gas processing plant of an alternative prior art system according to reissue U.S. Pat. No. 33,408;

FIG. 3 is a flow diagram of a cryogenic expansion natural gas processing plant of an alternative prior art system according to U.S. Pat. No. 4,617,039;

In the following explanation of the above figures, tables are provided summarizing flow rates calculated for representative process conditions. In the tables appearing herein, the values for flow rates (in pound moles per hour) have been rounded to the nearest whole number for convenience. The total stream rates shown in the tables include all nonhydrocarbon components and hence are generally larger than the sum of the stream flow rates for the hydrocarbon components. Temperatures indicated are approximate values rounded to the nearest degree. It should also be noted that the process design calculations performed for the purpose of comparing the processes depicted in the figures are based on the assumption of no heat leak from (or to) the surroundings to (or from) the process. The quality of commercially available insulating materials makes this a very reasonable assumption and one that is typically made by those skilled in the art.

DESCRIPTION OF THE PRIOR ART

Figure 1:
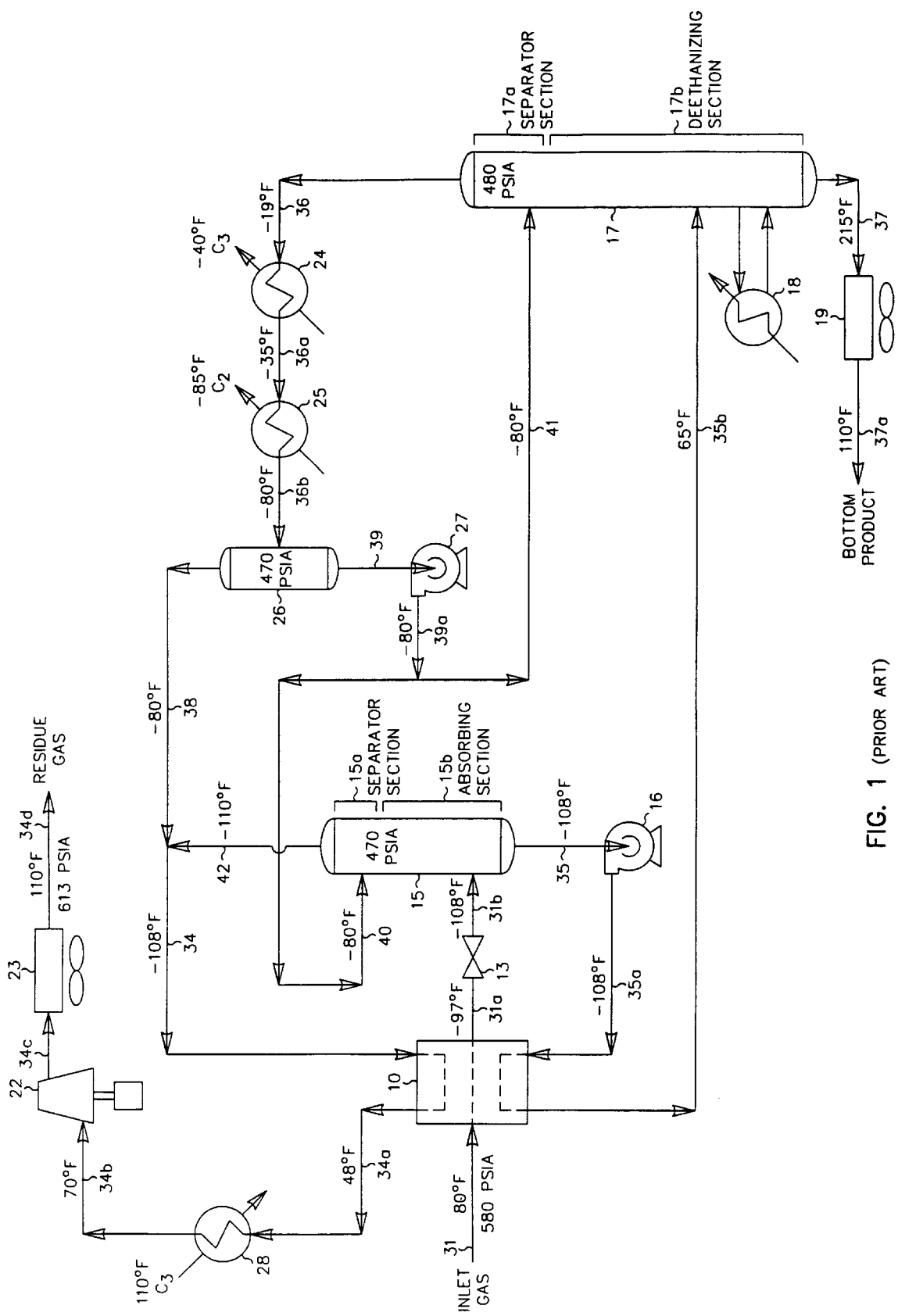

Referring now to FIG. 1, in a simulation of the prior art process described therein, inlet gas enters the plant at 80° F. and 580 psia as stream 31. If the inlet gas contains a concentration of sulfur compounds which would prevent the product streams from meeting specifications, the sulfur compounds are removed by appropriate pretreatment of the feed gas (not illustrated). In addition, the feed stream is usually dehydrated to prevent hydrate (ice) formation under cryogenic conditions. Solid desiccant has typically been used for this purpose.

The feed stream is cooled to −97° F. (stream 31a) in exchanger 10 by heat exchange with cold residue gas at −108° F. (stream 34) and with separator/absorber liquids at −108° F. (stream 35a). (The decision as to whether to use more than one heat exchanger for the indicated cooling services will depend on a number of factors including, but not limited to, inlet gas flow rate, heat exchanger size, stream temperatures, etc.).

In the previous application of this prior art process, the cooled feed stream 31a was subsequently distilled at pressure, as the feed stream was available at a lower pressure than in this example. Those skilled in the art will recognize that it is not possible to distill this stream effectively at the feed gas pressure used in this example. Accordingly, the cooled feed stream is first flash expanded through an appropriate expansion device, such as expansion valve 13, to the operating pressure (approximately 470 psia) of separator/absorber tower 15. During expansion the Joule-Thomson effect further cools the feed stream. In the process illustrated in FIG. 1, the expanded stream 31b leaving expansion valve 13 reaches a temperature of −108° F. and is supplied to absorbing section 15b in a lower region of separator/absorber tower 15. The liquid portion of the expanded stream commingles with liquids falling downward from absorbing section 15b and the combined liquid stream 35 exits the bottom of separator/absorber 15. The vapor portion of the expanded stream rises upward through absorbing section 15b and is contacted with cold liquid falling downward.

The separator/absorber tower 15 is a conventional distillation column containing a plurality of vertically spaced trays, one or more packed beds, or some combination of trays and packing. As is often the case in natural gas processing plants, the separator/absorber tower may consist of two sections. The upper section 15a is a separator wherein any vapor contained in the top feed is separated from its corresponding liquid portion, and wherein the vapor rising from the lower distillation or absorbing section 15b is combined with the vapor portion (if any) of the top feed to form the cold distillation stream 42 which exits the top of the tower. The lower, absorbing section 15b contains the trays and/or packing and provides the necessary contact between the liquids falling downward and the vapors rising upward to condense and absorb the propane and heavier components.

The combined liquid stream 35 leaves the bottom of the separator/absorber 15 at −108° F. It is supplied as a mid-column feed (stream 35b) to deethanizer 17 by pump 16 after it provides cooling of the feed gas in exchanger 10 as described earlier. The deethanizer in tower 17, operating at 480 psia, is also a conventional distillation column containing a plurality of vertically spaced trays, one or more packed beds, or some combination of trays and packing. The deethanizer tower may also consist of two sections: an upper section 17a wherein any vapor contained in the top feed is separated from its corresponding liquid portion, and wherein the vapor rising from the lower distillation or deethanizing section 17b is combined with the vapor portion (if any) of the top feed to form distillation stream 36 which exits the top of the tower; and a lower, deethanizing section 17b that contains the trays and/or packing to provide the necessary contact between the liquids falling downward and the vapors rising upward. The deethanizing section 17b also includes a reboiler 18 which heats and vaporizes a portion of the liquid at the bottom of the column to provide the stripping vapors which flow up the column to strip the liquid product, stream 37, of methane and $C_2$ components. A typical specification for the bottom liquid product is to have an ethane to propane ratio of 0.02:1 on a molar basis. The liquid product stream 37 exits the bottom of the tower at 215° F. and is cooled to 110° F. (stream 37a) in heat exchanger 19 before flowing to storage.

The overhead vapor stream 36 leaves deethanizer tower 17 at −19° F. and is partially condensed by heat exchangers 24 and 25 through the use of −40° F. propane refrigerant and −85° F. ethane refrigerant, respectively. The partially condensed stream 36b, now at −80° F. and 470 psia, enters reflux drum 26 and is separated into vapor stream 38 and condensed liquid stream 39. Pump 27 is used to supply a portion of the condensed liquid (stream 41) to the top of deethanizer tower 17 as reflux. The remaining portion of the condensed liquid (stream 40) is supplied by pump 27 to the top of separator/absorber 15 as the cold liquid that contacts the vapors rising upward through absorbing section 15b as described earlier.

Reflux drum 26 is operated at essentially the same pressure as separator/absorber 15, i.e., about 10 psi below the operating pressure of deethanizer 17. This allows the vapor portion (stream 38) of the partially condensed deethanizer overhead (stream 36b) to combine with the cold distillation stream 42 from the top of separator/absorber 15 to form the cold residue gas stream 34. The residue gas stream passes countercurrently to the incoming feed gas in heat exchanger 10 where it is heated to 48° F. (stream 34a). The residue gas is then used to subcool the high pressure propane refrigerant in heat exchanger 28, heating the residue gas to 70° F. (stream 34b) before it is re-compressed in one stage. (For this case, this heat exchanger reduces refrigeration compression at the expense of residue gas compression, but results in a net lower overall power consumption.) Compressor 22 is driven by a supplemental power source to compress the residue gas (stream 34c) to sales line pressure (usually on the order of the inlet pressure). After cooling in discharge cooler 23, the residue gas product (stream 34d) flows to the sales gas pipeline at 110° F. and 613 psia.

A summary of stream flow rates and energy consumption for the process illustrated in FIG. 1 is set forth in the following table:

TABLE I (FIG. 1)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 35 | 6349 | 2026 | 833 | 439 | 9770 |
| 36 | 10952 | 6957 | 43 | 0 | 18255 |
| 38 | 5135 | 704 | 1 | 0 | 5916 |
| 41 | 4603 | 4947 | 33 | 0 | 9764 |
| 40 | 1214 | 1306 | 9 | 0 | 2575 |
| 42 | 76205 | 3408 | 54 | 0 | 80645 |
| 34 | 81340 | 4112 | 55 | 0 | 86561 |
| 37 | 0 | 16 | 823 | 439 | 1279 |

| Recoveries* | |
|---|---|
| Propane | 93.71% |
| Butanes+ | 100.00% |
| Horsepower | |
| Residue Compression | 12,973 |
| Refrigeration Compression | 16,562 |
| Total | 29,535 |
| Utility Heat, MBTU/Hr | |
| Deethanizer Reboiler | 29,976 |

*(Based on un-rounded flow rates)

In the prior art illustrated in FIG. 1, the residue gas (stream 34) consists of both the separator/absorber overhead (stream 42) and the vapor (stream 38) remaining after partial condensation of the deethanizer overhead (stream 36). As such, the deethanizer overhead must be cooled to a sufficiently low temperature (−80° F.) so that essentially all of the propane it contains is condensed and does not escape in stream 38, and so that the portion (stream 40) of the resulting condensed liquid that is fed to the top of separator/absorber 15 is cold enough to condense nearly all of the propane contained in the vapor portion of the cooled expanded feed stream 31b as it is contacted in absorbing section 15b. Since there are no process streams available at suitable temperatures to provide the cooling needed to partially condense the deethanizer overhead, external mechanical refrigeration (evaporation of propane refrigerant in heat exchanger 24 and ethane refrigerant in heat exchanger 25) must be used for this duty, adding a substantial amount of utility consumption for refrigerant compression.

Figure 2:
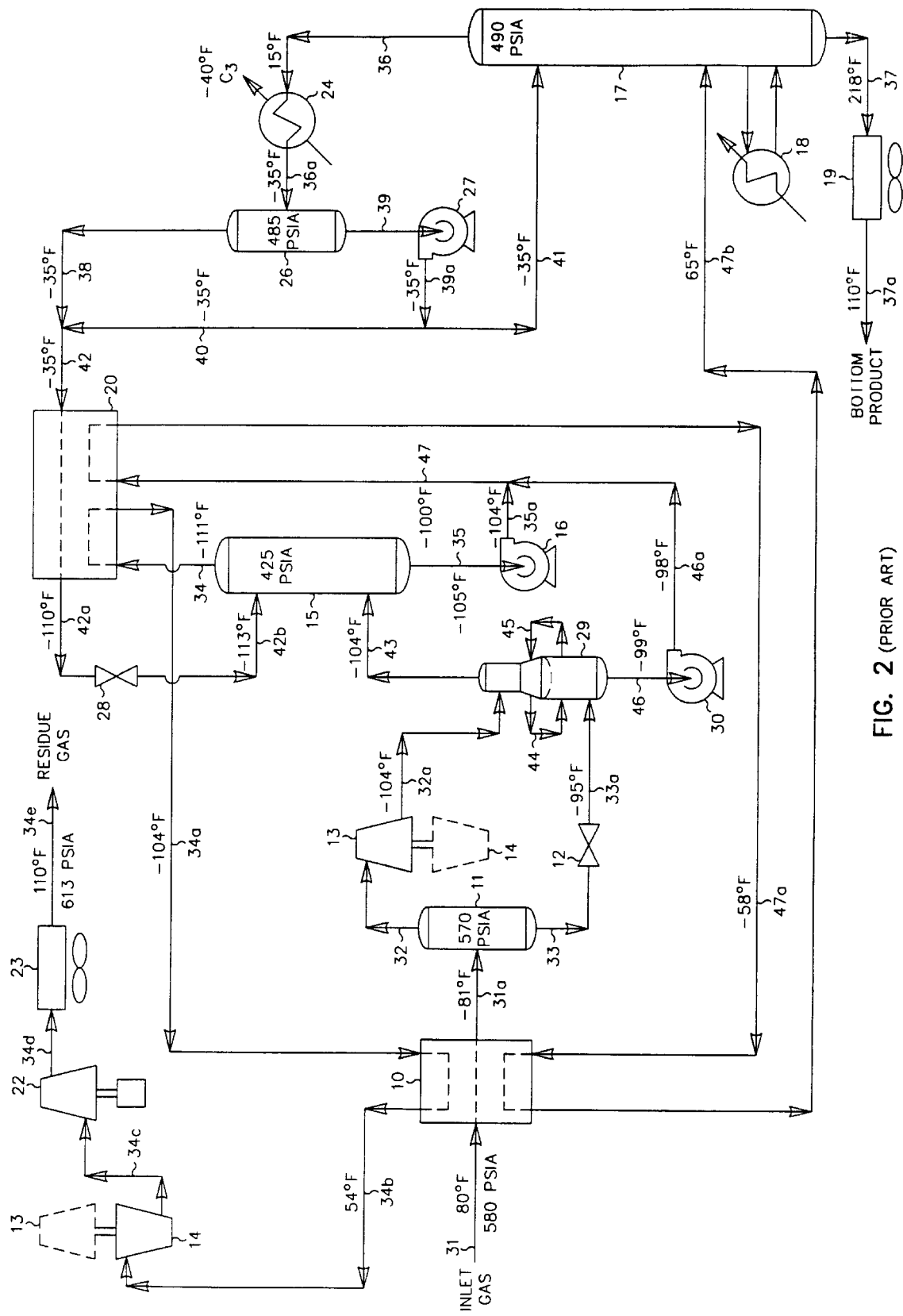

One way to achieve the desired propane recovery while lowering the utility consumption is to revise the manner in which the cold liquid feeding the top of the separator/absorber is created, so that the cooling load can be better matched to the temperature levels of the available process streams. FIG. 2 represents an alternative prior art process in accordance with reissue U.S. Pat. No. 33,408 that accomplishes this goal. The process of FIG. 2 has been applied to the same feed gas composition and conditions as described above for FIG. 1. In the simulation of this process, as in the simulation for the process of FIG. 1, operating conditions were selected to minimize the energy consumption for a given level of propane recovery.

The feed stream 31 is cooled in exchanger 10 by heat exchange with cool residue gas at −104° F. (stream 34a) and with deethanizer feed liquids at −58° F. (stream 47a). The cooled stream 31a enters separator 11 at −81° F. and 570 psia where the vapor (stream 32) is separated from the condensed liquid (stream 33).

The vapor (stream 32) from separator 11 enters a work expansion machine 13 in which mechanical energy is extracted from this portion of the high pressure feed. The machine 13 expands the vapor substantially isentropically from a pressure of about 570 psia to a pressure of about 425 psia (the operating pressure of separator/absorber 15), with the work expansion cooling the expanded stream 32a to a temperature of approximately −104° F. The typical commercially available expanders are capable of recovering on the order of 80–85% of the work theoretically available in an ideal isentropic expansion. The work recovered is often used to drive a centrifugal compressor (such as item 14), that can be used to re-compress the residue gas (stream 34b), for example.

The expanded and partially condensed stream 32a enters the upper section of intermediate separator 29. The separator liquid (stream 33) is likewise expanded to 425 psia by expansion valve 12, cooling stream 33 to −95° F. (stream 33a) before it enters the lower section of intermediate separator 29. The portion of stream 33a that vaporizes during the flash expansion (stream 45) leaves the lower section of intermediate separator 29 and enters the upper section to join the vapor portion of expanded stream 32a, forming combined vapor stream 43 that then flows to separator/absorber 15. The portion of stream 32a that condenses during expansion (stream 44) leaves the upper section of intermediate separator 29 and enters the lower section to join the liquid portion of flash expanded stream 33a, forming combined liquid stream 46 that then flows to pump 30.

The combined vapor stream 43 enters the lower section of separator/absorber 15 at −104° F. and 425 psia. As the vapor stream rises upward through the tower, it is contacted by the cold liquid falling downward to condense and absorb the propane and heavier components. The liquids from the bottom of separator/absorber 15 (stream 35) are pumped by pump 16 (stream 35a) to join the combined liquid stream 46a leaving pump 30, forming deethanizer feed stream 47. Stream 47 is heated from −100° F. to −58° F. (stream 47a) as it provides cooling in heat exchanger 20, and from −58° F. to 65° F. (stream 47b) as it provides cooling in heat exchanger 10. Stream 47b is then supplied to deethanizer 17 (operating at 490 psia) as a mid-column feed to be stripped of its methane and $C_2$ components. The liquid product stream 37 exits the bottom of the deethanizer at 218° F. and is cooled to 110° F. (stream 37a) in heat exchanger 19 before flowing to storage.

The overhead vapor stream 36 leaves deethanizer tower 17 at 15° F. and is partially condensed by heat exchanger 24 through the use of −40° F. propane refrigerant. The partially condensed stream 36a, now at −35° F. and 485 psia, enters reflux drum 26 and is separated into vapor stream 38 and condensed liquid stream 39. Pump 27 is used to supply a portion of the condensed liquid (stream 41) to the top of deethanizer tower 17 as reflux. The remaining portion of the condensed liquid (stream 40) leaving pump 27 joins with stream 38 to form combined stream 42.

Combined stream 42 passes through heat exchanger 20 in heat exchange relation with the separator/absorber overhead vapor stream 34 and the deethanizer feed stream 47, resulting in cooling and substantial condensation of the stream. The substantially condensed stream 42a at −110° F. is then flash expanded through an appropriate expansion device, such as expansion valve 28, to the operating pressure (approximately 425 psia) of separator/absorber tower 15. Reflux drum 26 is operated significantly above the operating pressure of separator/absorber 15 (about 60 psi). As a result, a portion of the stream 42a is vaporized during expansion, providing further cooling of the total stream. In the process illustrated in FIG. 2, the expanded stream 42b leaving expansion valve 28 reaches a temperature of −113° F. and is then supplied to the separator section in separator/absorber tower 15 as the cold liquid that contacts the vapors rising upward through the absorbing section.

The distillation stream leaving the top of separator/absorber 15 at −111° F. is the cold residue gas stream 34. The residue gas stream passes countercurrently to the combined stream 42 in heat exchanger 20 and is warmed to −104° F. (stream 34a) as it provides cooling and substantial condensation of the combined stream. The residue gas is further warmed to 54° F. (stream 34b) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34d) to sales line pressure. After cooling in discharge cooler 23, the residue gas product (stream 34e) flows to the sales gas pipeline at 110° F. and 613 psia.

A summary of stream flow rates and energy consumption for the process illustrated in FIG. 2 is set forth in the following table:

TABLE II (FIG. 2)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 79835 | 3575 | 512 | 103 | 85051 |
| 33 | 1505 | 553 | 366 | 336 | 2789 |
| 43 | 79214 | 3147 | 280 | 21 | 83671 |
| 46 | 2126 | 981 | 598 | 418 | 4169 |
| 35 | 1106 | 506 | 287 | 21 | 1945 |
| 36 | 4839 | 5003 | 405 | 0 | 10395 |
| 38 | 3087 | 1153 | 31 | 0 | 4335 |
| 41 | 1607 | 3532 | 343 | 0 | 5560 |
| 40 | 145 | 318 | 31 | 0 | 500 |
| 34 | 81340 | 4112 | 55 | 0 | 86561 |
| 37 | 0 | 16 | 823 | 439 | 1279 |

Recoveries*

| | |
|---|---|
| Propane | 93.69% |
| Butanes+ | 100.00% |

TABLE II-continued (FIG. 2)
Stream Flow Summary - (Lb. Moles/Hr)

| Horsepower | |
|---|---|
| Residue Compression | 13,429 |
| Refrigeration Compression | 6,690 |
| Total | 20,119 |
| Utility Heat, MBTU/Hr | |
| Deethanizer Reboiler | 23,626 |

*(Based on un-rounded flow rates)

Comparison of the utility consumptions in Table II above for the FIG. 2 process with those in Table I for the FIG. 1 process shows that the FIG. 2 process does substantially reduce both the refrigeration compression load and the deethanizer reboiler duty over that of the FIG. 1 process for a given propane recovery level. This is accomplished by using process streams to provide the cooling required for the cold liquid stream feeding the top of separator/absorber tower 15. The FIG. 2 process still requires the use of external mechanical refrigeration (evaporation of propane refrigerant in heat exchanger 24) to partially condense the deethanizer overhead (stream 36). As such, a plant design based on the FIG. 2 process must incur the capital cost associated with the installation of the propane compression-refrigeration system.

Figure 3:
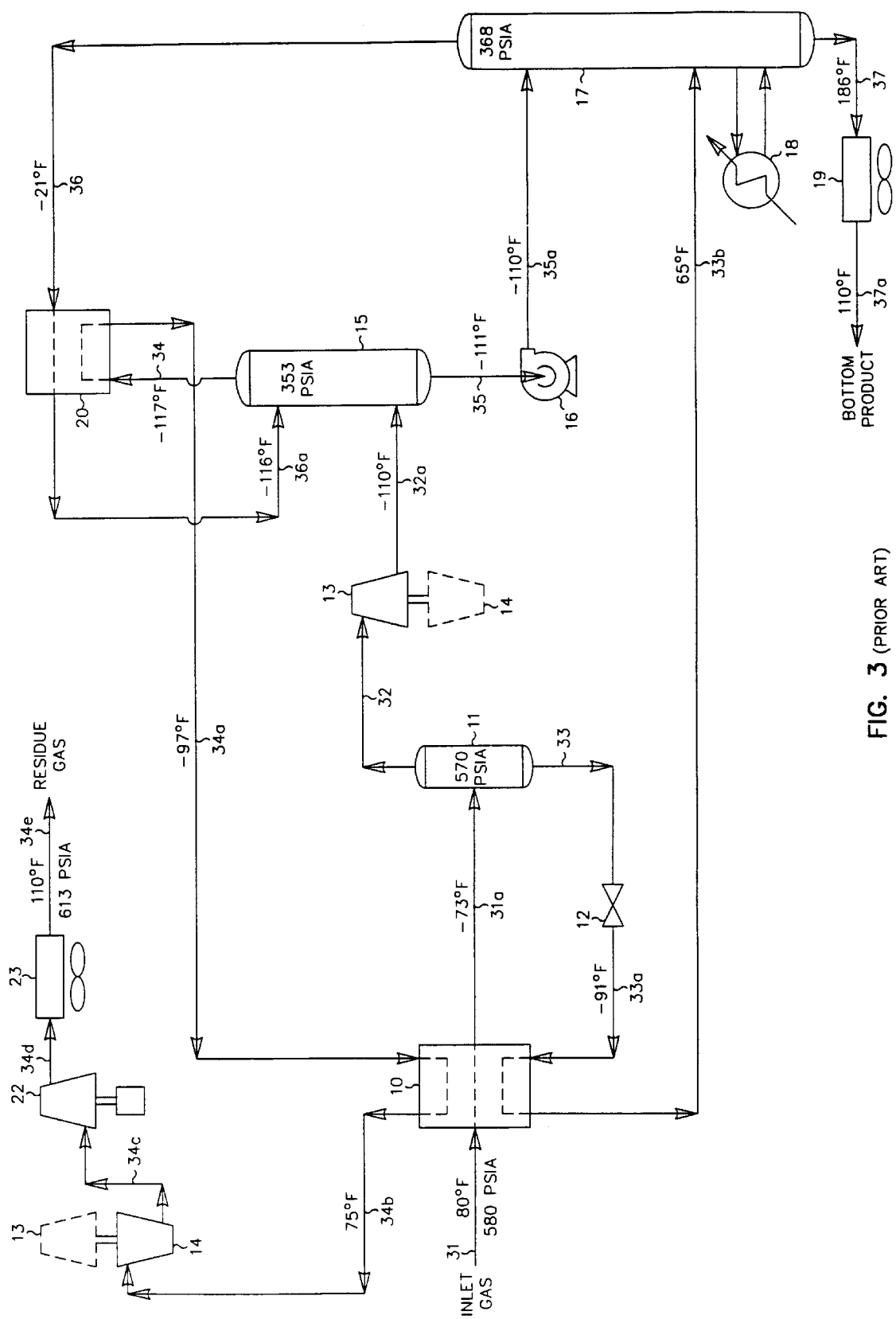

FIG. 3 represents an alternative prior art process in accordance with U.S. Pat. No. 4,617,039 that achieves the desired propane recovery while using a simpler, less costly plant arrangement. The process of FIG. 3 is based on the same feed gas composition and conditions as described above for FIGS. 1 and 2. In the simulation of this process, the feed stream 31 is cooled in exchanger 10 by heat exchange with cool residue gas at −97° F. (stream 34a) and with separator liquids at −91° F. (stream 33a). The cooled stream 31a enters separator 11 at −73° F. and 570 psia where the vapor (stream 32) is separated from the condensed liquid (stream 33).

The vapor (stream 32) from separator 11 enters a work expansion machine 13 in which mechanical energy is extracted from this portion of the high pressure feed. The machine 13 expands the vapor substantially isentropically from a pressure of about 570 psia to a pressure of about 353 psia (the operating pressure of separator/absorber 15), with the work expansion cooling the expanded stream 32a to a temperature of approximately −110° F. The expanded and partially condensed stream 32a enters the lower section of separator/absorber 15. The liquid portion of the expanded stream commingles with liquids falling downward from the absorbing section and the combined liquid stream 35 exits the bottom of separator/absorber 15 at −111° F. The vapor portion of the expanded stream rises upward through the absorbing section and is contacted with cold liquid falling downward to condense and absorb the propane and heavier components.

The combined liquid stream 35 from the bottom of the separator/absorber 15 is supplied as a cold top column feed (stream 35a) to deethanizer 17 by pump 16. The separator liquid (stream 33) is flash expanded to slightly above the 368 psia operating pressure of deethanizer 17 by expansion valve 12, cooling stream 33 to −91° F. (stream 33a) before it provides cooling to the incoming feed gas as described earlier. Stream 33b, now at 65° F., then enters deethanizer 17 at a mid-column feed point to be stripped of its methane and $C_2$ components. The liquid product stream 37 exits the bottom of the deethanizer at 186° F. and is cooled to 110° F. (stream 37a) in heat exchanger 19 before flowing to storage.

The operating pressure in deethanizer 17 is maintained slightly above the operating pressure of separator/absorber 15. This allows the deethanizer overhead vapor (stream 36) to pressure flow through heat exchanger 20 and thence into the upper section of separator/absorber 15. In heat exchanger 20, the deethanizer overhead at −21° F. is directed in heat exchange relation with the overhead (stream 34) from separator/absorber 15, cooling the stream to −116° F. (stream 36a) and partially condensing it. The partially condensed stream is then supplied to the separator section in separator/absorber tower 15, so that its condensed liquid is separated to become the cold liquid that contacts the vapors rising upward through the absorbing section.

The distillation stream leaving the top of separator/absorber 15 at −117° F. is the cold residue gas stream 34. The residue gas stream passes countercurrently to deethanizer overhead stream 36 in heat exchanger 20 and is warmed to −97° F. (stream 34a) as it provides cooling and partial condensation of the deethanizer overhead stream. The residue gas is further warmed to 75° F. (stream 34b) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34d) to sales line pressure. After cooling in discharge cooler 23, the residue gas product (stream 34e) flows to the sales gas pipeline at 110° F. and 613 psia.

A summary of stream flow rates and energy consumption for the process illustrated in FIG. 3 is set forth in the following table:

TABLE III (FIG. 3)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 80476 | 3792 | 623 | 149 | 86078 |
| 33 | 864 | 336 | 255 | 290 | 1762 |
| 35 | 2199 | 1261 | 689 | 156 | 4359 |
| 36 | 3063 | 1581 | 121 | 7 | 4843 |
| 34 | 81340 | 4112 | 55 | 0 | 86562 |
| 37 | 0 | 16 | 823 | 439 | 1278 |

| Recoveries* | |
|---|---|
| Propane | 93.70% |
| Butanes+ | 99.85% |
| Horsepower | |
| Residue Compression Utility Heat, MBTU/Hr | 21,210 |
| Deethanizer Reboiler | 22,298 |

*(Based on un-rounded flow rates)

Comparison of the utility consumptions in Table III above for the FIG. 3 process with those in Table II for the FIG. 2 process shows that the FIG. 3 process achieves the desired propane recovery level for approximately the same total compression load and deethanizer reboiler duty as that of the FIG. 2 process. The decision whether to use the simpler, less costly FIG. 3 process rather than the FIG. 2 process will often depend on such factors as the relative costs of utility heat and compression horsepower, plant size, etc. It should be noted in passing that the success of the FIG. 3 process depends on the absorption cooling effect that occurs inside separator/absorber 15, wherein the saturation of the vapors rising upward through the tower by vaporization of liquid methane and ethane contained in stream 36a provides refrigeration to the tower. Note that, as a result, both the vapor leaving the overhead of the tower and the liquids leaving the bottom of the tower are colder than the respective feed streams at those ends of the tower. This absorption cooling effect allows the tower overhead (stream 34) to provide the cooling needed in heat exchanger 20 to partially condense the deethanizer overhead (stream 36) without operating deethanizer 17 at a pressure significantly higher than that of the separator/absorber 15. This was not the case in the FIG. 2 process, where Joule-Thomson cooling of the condensed deethanizer overhead stream was needed to provide the temperature driving force that allowed the heat exchange to occur.

DESCRIPTION OF THE INVENTION

EXAMPLE 1

Figure 4:
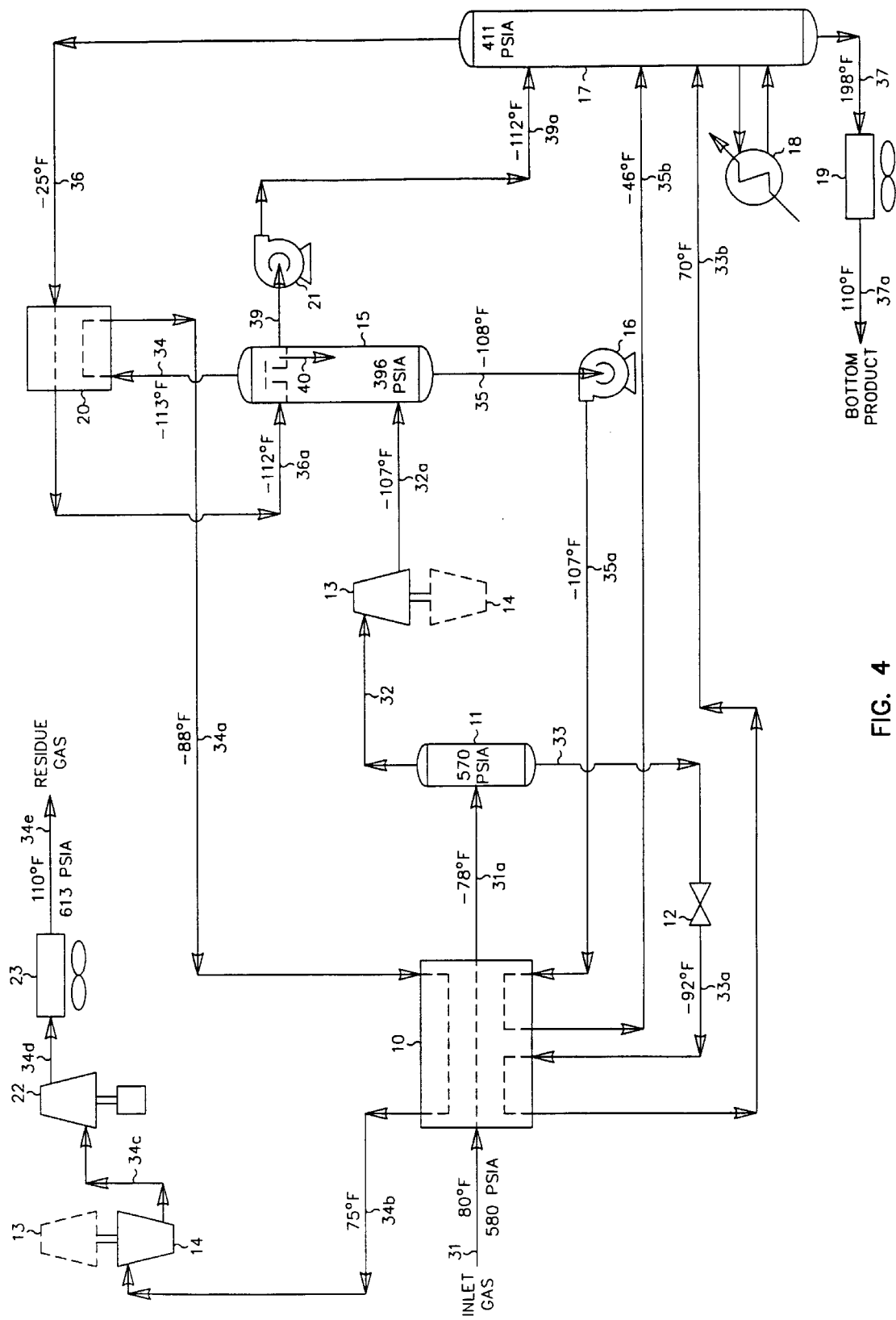
FIG. 4 is a flow diagram of a natural gas processing plant in accordance with the present invention.

FIG. 4 illustrates a flow diagram of a process in accordance with the present invention. The feed gas composition and conditions considered in the process presented in FIG. 4 are the same as those in FIGS. 1 through 3. Accordingly, the FIG. 4 process can be compared with the FIGS. 1 through 3 processes to illustrate the advantages of the present invention.

In the simulation of the FIG. 4 process, feed gas enters at 80° F. and a pressure of 580 psia as stream 31. The feed stream 31 is cooled in exchanger 10 by heat exchange with cool residue gas at −88° F. (stream 34a), with separator liquids at −92° F. (stream 33a), and with separator/absorber liquids at −107° F. (stream 35a). The cooled stream 31a enters separator 11 at −78° F. and 570 psia where the vapor (stream 32) is separated from the condensed liquid (stream 33).

The vapor (stream 32) from separator 11 enters a work expansion machine 13 in which mechanical energy is extracted from this portion of the high pressure feed. The machine 13 expands the vapor substantially isentropically from a pressure of about 570 psia to a pressure of about 396 psia (the operating pressure of separator/absorber 15), with the work expansion cooling the expanded stream 32a to a temperature of approximately −107° F. The expanded and partially condensed stream 32a enters the lower section of separator/absorber 15. The liquid portion of the expanded stream commingles with liquids falling downward from the absorbing section and the combined liquid stream 35 exits the bottom of separator/absorber 15 at −108° F. The vapor portion of the expanded stream rises upward through the absorbing section and is contacted with cold liquid falling downward to condense and absorb the propane and heavier components.

The combined liquid stream 35 from the bottom of the separator/absorber 15 is routed to heat exchanger 10 by pump 16 where it (stream 35a) is heated as it provides cooling of the incoming feed gas as described earlier. The combined liquid stream is heated to −46° F., partially vaporizing stream 35b before it is supplied as a mid-column feed to deethanizer 17. The separator liquid (stream 33) is flash expanded to slightly above the 411 psia operating pressure of deethanizer 17 by expansion valve 12, cooling stream 33 to −92° F. (stream 33a) before it provides cooling to the incoming feed gas as described earlier. Stream 33b, now at 70° F., then enters deethanizer 17 at a lower mid-column feed point. In the deethanizer, streams 35b and 33b are stripped of their methane and $C_2$ components. The resulting liquid product stream 37 exits the bottom of the deethanizer at 198° F. and is cooled to 110° F. (stream 37a) in heat exchanger 19 before flowing to storage.

The operating pressure in deethanizer 17 is maintained slightly above the operating pressure of separator/absorber 15. This allows the deethanizer overhead vapor (stream 36) to pressure flow through heat exchanger 20 and thence into the upper section of separator/absorber 15. In heat exchanger 20, the deethanizer overhead at −25° F. is directed in heat exchange relation with the overhead (stream 34) from separator/absorber 15, cooling the stream to −112° F. (stream 36a) and partially condensing it. The partially condensed stream is then supplied to the separator section in separator/absorber tower 15 where the condensed liquid is separated from the uncondensed vapor. The uncondensed vapor combines with the vapor rising from the lower absorbing section to form the cold distillation stream 34 leaving the upper region of separator/absorber 15. The condensed liquid is divided into two portions. One portion, stream 40, is routed to the lower absorbing section of separator/absorber 15 as the cold liquid that contacts the vapors rising upward through the absorbing section. The other portion, stream 39, is supplied to deethanizer 17 as reflux by pump 21, with reflux stream 39a flowing to a top feed point on deethanizer 17 at −112° F.

The distillation stream leaving the top of separator/absorber 15 at −113° F. is the cold residue gas stream 34. The residue gas stream passes countercurrently to deethanizer overhead stream 36 in heat exchanger 20 and is warmed to −88° F. (stream 34a) as it provides cooling and partial condensation of the deethanizer overhead stream. The residue gas is further warmed to 75° F. (stream 34b) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34d) to sales line pressure. After cooling in discharge cooler 23, the residue gas product (stream 34e) flows to the sales gas pipeline at 110° F. and 613 psia.

A summary of stream flow rates and energy consumption for the process illustrated in FIG. 4 is set forth in the table below:

TABLE IV (FIG. 4)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 80084 | 3656 | 549 | 117 | 85436 |
| 33 | 1256 | 472 | 329 | 322 | 2404 |
| 35 | 2277 | 1139 | 597 | 117 | 4182 |
| 36 | 4378 | 2084 | 135 | 0 | 6695 |
| 40 | 2676 | 1549 | 102 | 0 | 4395 |
| 39 | 845 | 489 | 32 | 0 | 1388 |
| 34 | 81340 | 4112 | 55 | 0 | 86561 |
| 37 | 0 | 16 | 823 | 439 | 1279 |

Recoveries*

| | |
|---|---|
| Propane | 93.68% |
| Butanes+ | 100.00% |

TABLE IV-continued (FIG. 4)
Stream Flow Summary - (Lb. Moles/Hr)

Horsepower

| | |
|---|---|
| Residue Compression | 17,536 |
| Utility Heat, MBTU/Hr | |
| Deethanizer Reboiler | 16,270 |

*(Based on un-rounded flow rates)

Comparison of the utility consumptions of the prior art processes displayed in Tables I, II and III with the utility consumptions of the present invention displayed in Table IV shows that the present invention maintains the desired $C_3$ component recovery while substantially reducing both the compression horsepower and the utility heat requirement. The compression horsepower is more than twelve percent lower than any of the prior art processes, while the utility heat requirement is more than twenty-seven percent lower than any of the prior art processes.

Comparing the present invention to the prior art process displayed in FIG. 3, note the temperatures of the separator/absorber liquids (stream 35a in FIG. 3 and stream 35b in FIG. 4) at the feed point to deethanizer 17. In the FIG. 3 process, these liquids are fed to the deethanizer as a cold top feed. However, the temperature of the deethanizer overhead vapor, −21° F., is much warmer than the −110° F. feed temperature of stream 35a, indicating that the top feed is much colder than necessary to maintain the desired propane and heavier component concentration in the tower overhead. In the FIG. 4 process, the feed stream (stream 35b) enters the deethanizer at −46° F. at a lower feed point. This is much closer to the −25° F. temperature of its deethanizer overhead vapor stream, indicating a better match to the feed conditions needed to achieve the desired propane and heavier component content of the overhead. As a result, only a small reflux stream, stream 39a, is needed for the top feed to deethanizer 17 in the FIG. 4 process. The much lower reboiler duty for the FIG. 4 process is a further indication of the better match between tower feed temperatures and the desired tower product streams.

By supplying the separator/absorber liquids to the FIG. 4 deethanizer at a more optimal temperature, not only is the efficiency of the deethanizer improved (as reflected in its lower reboiler duty), the refrigeration potential of these liquids can be captured at a temperature level that allows providing a portion of the process cooling duty. With these liquids helping cool the incoming feed gas in heat exchanger 10, the cooling that the residue gas (stream 34a) must supply in heat exchanger 10 is reduced. As a result, the residue gas can enter heat exchanger 10 at a warmer temperature, which in turn allows operating the FIG. 4 separator/absorber and deethanizer at higher pressures. Accordingly, the residue gas enters compressor 14 at a higher pressure in the FIG. 4 process and less compression horsepower is therefore needed to deliver the residue gas to pipeline pressure.

EXAMPLE 2

Figure 5:
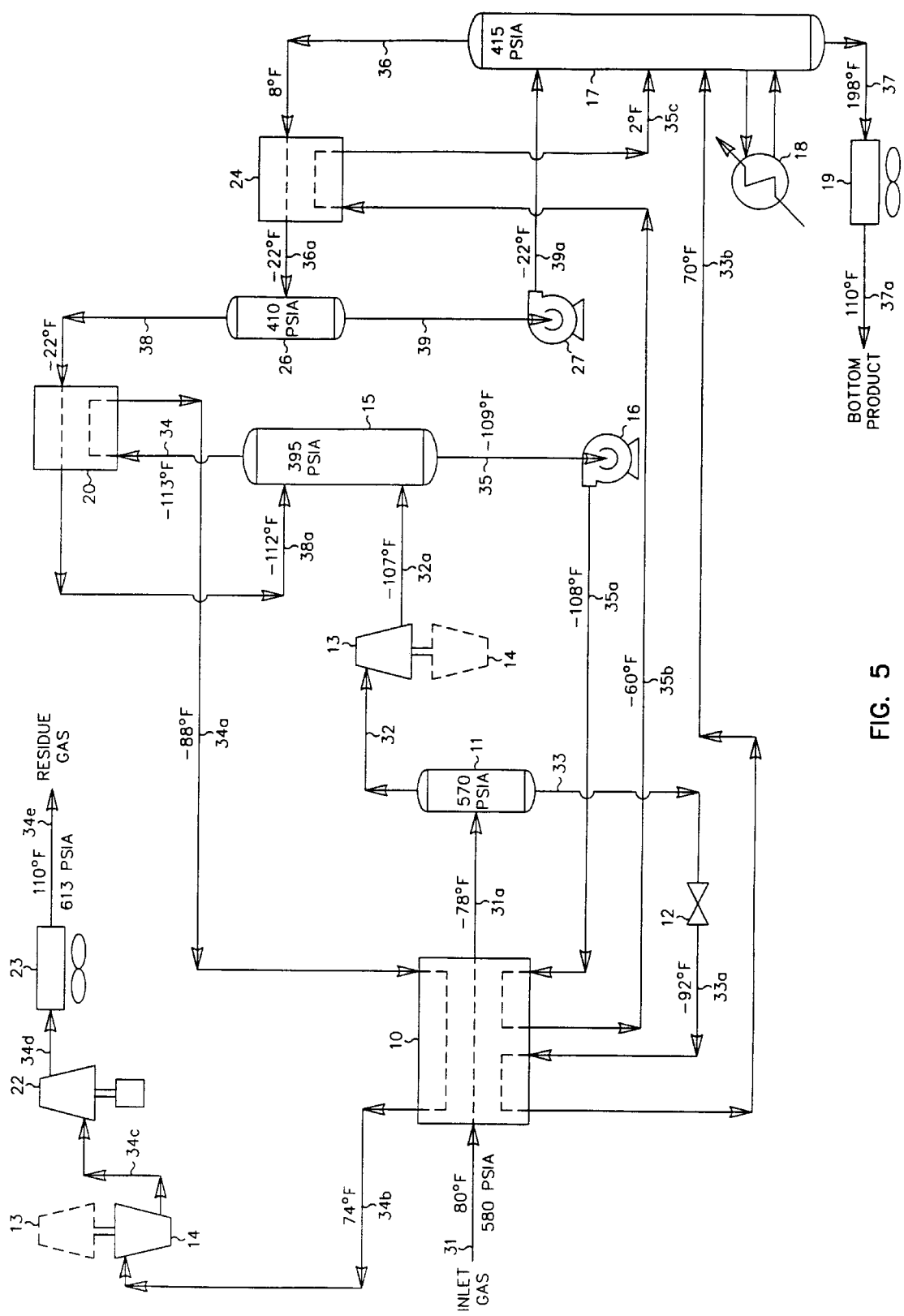
FIG. 5 is a flow diagram illustrating an alternative means of application of the present invention to a natural gas stream.

FIG. 4 represents the preferred embodiment of the present invention for the temperature and pressure conditions shown because it typically provides the simplest plant arrangement for a given $C_3$ component recovery level. A slightly more complex design that maintains the same $C_3$ component recovery for essentially the same utility consumption can be achieved using another embodiment of the present invention as illustrated in the FIG. 5 process. The feed gas composition and conditions considered in the process presented in FIG. 5 are the same as those in FIGS. 1 through 4. Accordingly, FIG. 5 can be compared with the FIGS. 1 through 3 processes to illustrate the advantages of the present invention, and can likewise be compared to the embodiment displayed in FIG. 4.

In the simulation of the FIG. 5 process, the feed gas cooling and expansion scheme is much the same as that used in FIG. 4. The difference lies in the disposition of the vapor distillation stream 36 leaving the overhead of deethanizer 17. Referring to FIG. 5, stream 36 at 8° F. flows to heat exchanger 24 and is directed in heat exchange relation with the partially warmed combined liquid stream (stream 35b) pumped from separator/absorber tower 15, cooling stream 36 and partially condensing it. The partially condensed stream 36a enters reflux drum 26 at −22° F. and 410 psia where the uncondensed vapor (stream 38) is separated from the condensed liquid (stream 39). The condensed liquid is returned to deethanizer 17 as reflux (stream 39a) by reflux pump 27, entering the deethanizer at −22° F. at a top feed point. The further warmed combined liquid stream (stream 35c) leaving heat exchanger 24 flows to deethanizer 17 at 2° F. and enters at a mid-column feed point. In the deethanizer, streams 35c and 33b (entering at a lower mid-column feed point) are stripped of their methane and $C_2$ components. The resulting liquid product stream 37 exits the bottom of the deethanizer at 198° F. and is cooled to 110° F. (stream 37a) in heat exchanger 19 before flowing to storage.

The operating pressure of reflux drum 26 is maintained slightly above the operating pressure of separator/absorber 15. This allows the uncondensed vapor (stream 38) to pressure flow through heat exchanger 20 and thence into the upper section of separator/absorber 15. In heat exchanger 20, the vapor stream at −22° F. is directed in heat exchange relation with the overhead (stream 34) from separator/absorber 15, cooling the stream to −112° F. (stream 38a) and partially condensing it. The partially condensed stream is then supplied to the separator section in separator/absorber tower 15, so that its condensed liquid is separated to become the cold liquid that contacts the vapors rising upward through the absorbing section.

The distillation stream leaving the top of separator/absorber 15 at −113° F. is the cold residue gas stream 34. The residue gas stream passes countercurrently to vapor stream 38 in heat exchanger 20 and is warmed to −88° F. (stream 34a) as it provides cooling and partial condensation of the stream. The residue gas is further warmed to 74° F. (stream 34b) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34d) to sales line pressure. After cooling in discharge cooler 23, the residue gas product (stream 34e) flows to the sales gas pipeline at 110° F. and 613 psia.

A summary of stream flow rates and energy consumptions for the process illustrated in FIG. 5 is set forth in the table below:

TABLE V (FIG. 5)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 80098 | 3661 | 552 | 118 | 85459 |
| 33 | 1242 | 467 | 326 | 321 | 2381 |
| 35 | 3136 | 1641 | 659 | 119 | 5627 |
| 36 | 4836 | 3457 | 567 | 5 | 8986 |
| 38 | 4378 | 2092 | 162 | 1 | 6729 |
| 39 | 458 | 1365 | 405 | 4 | 2257 |
| 34 | 81340 | 4112 | 55 | 0 | 86561 |
| 37 | 0 | 16 | 823 | 439 | 1279 |

| Recoveries* | |
|---|---|
| Propane | 93.72% |
| Butanes+ | 99.99% |
| Horsepower | |
| Residue Compression | 17,580 |
| Utility Heat, MBTU/Hr | |
| Deethanizer Reboiler | 15,999 |

*(Based on un-rounded flow rates)

Comparison of the utility consumptions displayed in Tables I, II and III for the FIGS. 1, 2 and 3 processes with those displayed in Table V for the FIG. 5 process shows that this embodiment of the present invention also reduces the utility consumptions for a given $C_3$ component recovery level over that of the prior art process. The compression horsepower is more than twelve percent lower than any of the prior art processes, while the utility heat requirement is more than twenty-eight percent lower than any of the prior art processes. Comparison of the utility consumptions displayed in Tables IV and V for the FIG. 4 and FIG. 5 processes shows that the FIG. 5 embodiment of the present invention requires slightly more compression horsepower (about 0.25 percent) than the FIG. 4 embodiment, but uses about 1.7 percent less utility heat for the deethanizer reboiler. These two embodiments of the present invention have essentially the same total utility requirements. The choice of whether to include the additional equipment that the FIG. 5 process requires will generally depend on factors which include plant size and available equipment, as well as the relative costs of compression horsepower and utility heat.

EXAMPLE 3

Figure 6:
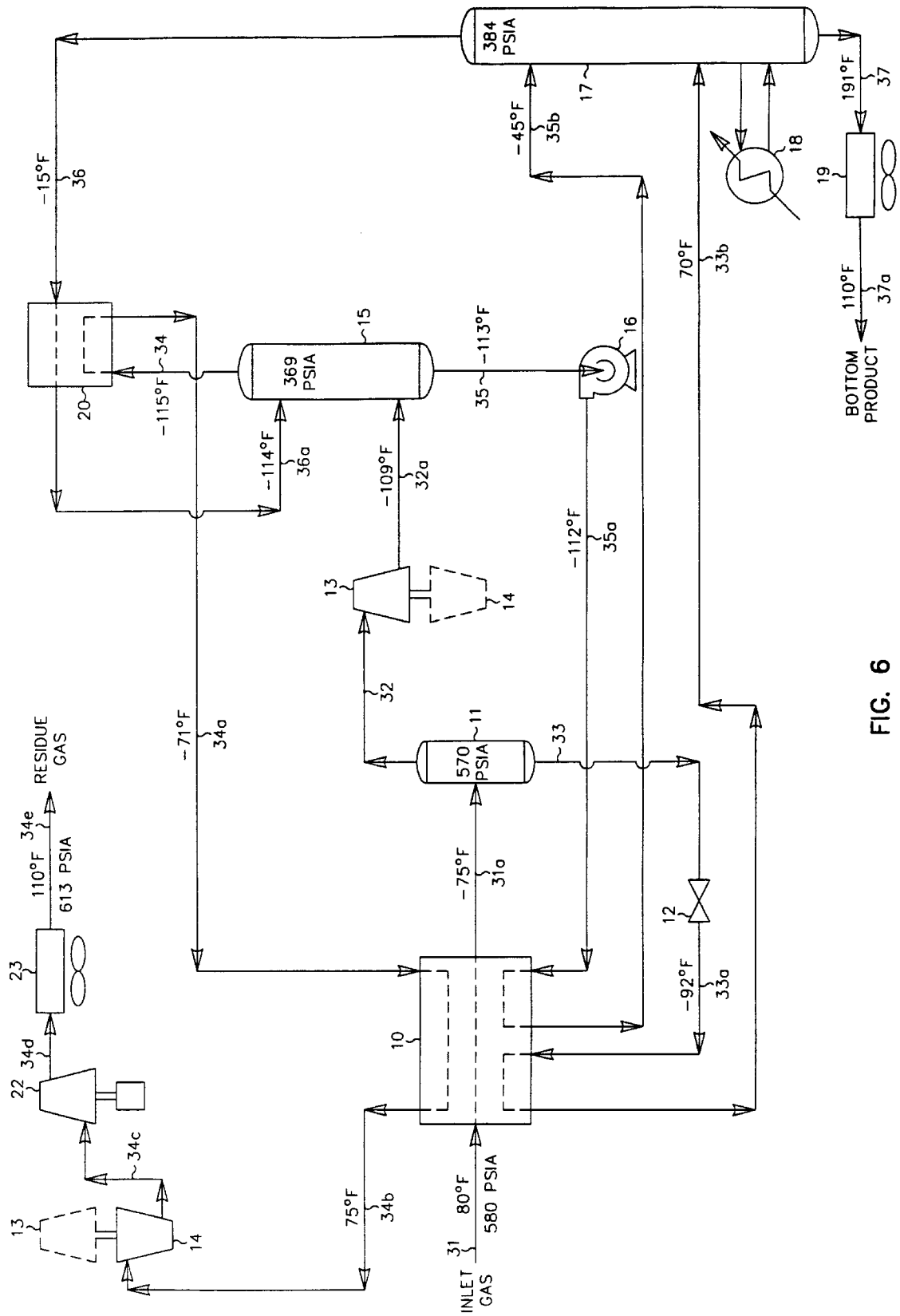
FIG. 6 is a flow diagram illustrating another alternative means of application of the present invention to a natural gas stream.

A third embodiment of the present invention is shown in FIG. 6, wherein a simpler embodiment of the present invention is applied. The feed gas composition and conditions considered in the process illustrated in FIG. 6 are the same as those in FIGS. 1 through 5.

In the simulation of the FIG. 6 process, the feed gas cooling and expansion scheme is essentially the same as that used in FIG. 4. The difference lies in the disposition of the combined liquid stream from separator/absorber 15 after it has been partially warmed (stream 35b) by providing cooling of the incoming feed gas in heat exchanger 10. Referring to FIG. 6, stream 35a from pump 16 is heated from −112° F. to −45° F. in heat exchanger 10 as it provides cooling of the incoming feed gas as described previously in Example 1. The heated stream, stream 35b, is then supplied to deethanizer 17 at a top column feed point, entering the tower at −45° F. to be stripped of its methane and $C_2$ components. The resulting liquid product stream 37 exits the bottom of the deethanizer at 191° F. and is cooled to 110° F. (stream 37a) in heat exchanger 19 before flowing to storage.

The operating pressure in deethanizer 17 is maintained slightly above the operating pressure of separator/absorber 15. This allows the deethanizer overhead vapor (stream 36) to pressure flow through heat exchanger 20 and thence into the upper section of separator/absorber 15. In heat exchanger 20, the deethanizer overhead at −15° F. is directed in heat exchange relation with the overhead (stream 34) from separator/absorber 15, cooling the stream to −114° F. (stream 36a) and partially condensing it. The partially condensed stream is then supplied to the separator section in separator/absorber tower 15, so that its condensed liquid is separated to become the cold liquid that contacts the vapors rising upward through the absorbing section.

The distillation stream leaving the top of separator/absorber 15 at −115° F. is the cold residue gas stream 34. The residue gas stream passes countercurrently to deethanizer overhead stream 36 in heat exchanger 20 and is warmed to −71° F. (stream 34a) as it provides cooling and partial condensation of the deethanizer overhead stream. The residue gas is further warmed to 75° F. (stream 34b) as it passes countercurrently to the incoming feed gas in heat exchanger 10. The residue gas is then re-compressed in two stages. The first stage is compressor 14 driven by expansion machine 13. The second stage is compressor 22 driven by a supplemental power source which compresses the residue gas (stream 34d) to sales line pressure. After cooling in discharge cooler 23, the residue gas product (stream 34e) flows to the sales gas pipeline at 110° F. and 613 psia.

A summary of stream flow rates and energy consumptions for the process illustrated in FIG. 6 is set forth in the table below:

TABLE VI (FIG. 6)
Stream Flow Summary - (Lb. Moles/Hr)

| Stream | Methane | Ethane | Propane | Butanes+ | Total |
|---|---|---|---|---|---|
| 31 | 81340 | 4128 | 878 | 439 | 87840 |
| 32 | 80347 | 3746 | 596 | 137 | 85861 |
| 33 | 993 | 382 | 282 | 302 | 1979 |
| 35 | 4995 | 2983 | 826 | 153 | 9080 |
| 36 | 5988 | 3349 | 285 | 17 | 9781 |
| 34 | 81340 | 4112 | 55 | 1 | 86562 |
| 37 | 0 | 16 | 823 | 438 | 1278 |

| Recoveries* | |
|---|---|
| Propane | 93.68% |
| Butanes+ | 99.83% |
| Horsepower | |
| Residue Compression | 20,215 |
| Utility Heat, MBTU/Hr | |
| Deethanizer Reboiler | 20,254 |

*(Based on un-rounded flow rates)

Comparison of the utility consumptions displayed in Tables I, II and III for the FIGS. 1, 2 and 3 processes with those displayed in Table VI for the FIG. 6 process shows that this embodiment of the present invention uses a lower total utility consumption for a given $C_3$ component recovery level than the prior art processes. The compression horsepower is essentially the same (about 0.5 percent higher) than the lowest value used by any of the prior art processes, while the utility heat requirement is more than nine percent lower than any of the prior art processes. Due to its simpler arrangement than the FIGS. 4 and 5 embodiments, the FIG. 6 embodiment of the present invention may offer capital cost advantages that outweigh its higher utility consumption compared to the other embodiments. The choice between the FIGS. 4a 5 and 6 embodiments of the present invention will often depend on factors such as plant size, available equipment, and the economic balance of capital cost versus operating cost.

Other Embodiments

In accordance with this invention, it is generally advantageous to design the separator/absorber to provide a contacting device composed of multiple theoretical separation stages. However, the benefits of the present invention can be achieved with as few as one theoretical stage, and it is believed that even the equivalent of a fractional theoretical stage may allow achieving these benefits. For instance, all or a part of the partially condensed stream leaving heat exchanger 20 and all or a part of the partially condensed stream from work expansion machine 13 can be combined (such as in the piping joining the expansion machine to the separator/absorber) and if thoroughly intermingled, the vapors and liquids will mix together and separate in accordance with the relative volatilities of the various components of the total combine d streams. In such an embodiment, the vapor-liquid mixture from heat exchanger 20 can be used without separation, or the liquid portion thereof may be separated. Such commingling of the two streams shall be considered for the purposes of this invention as constituting a contacting device. In another variation of the foregoing, the partially condensed stream from heat exchanger 20 can be separated, and then all or a part of the separated liquid supplied to the separator/absorber or mixed with the vapors fed thereto.

As described earlier in the preferred embodiment, the overhead vapors are partially condensed and used to absorb valuable $C_3$ components and heavier components from the vapors leaving the work expansion machine. However, the present invention is not limited to this embodiment. It may be advantageous, for instance, to treat only a portion of the outlet vapor from the work expansion machine in this manner, or to use only a portion of the overhead condensate as an absorbent, in cases where other design considerations indicate portions of the expansion machine outlet or overhead condensate should bypass the separator/absorber. Feed gas conditions, plant size, available equipment, or other factors may indicate that elimination of work expansion machine 13, or replacement with an alternate expansion device (such as an expansion valve), is feasible, or that total (rather than partial) condensation of the overhead stream in heat exchanger 20 is possible or is preferred. It should also be noted that the separator/absorber can be constructed either as a separate vessel or as a section of the deethanizer column.

In the practice of the present invention, there will necessarily be a slight pressure difference between the deethanizer and the separator/absorber which must be taken into account. If the overhead vapors pass through heat exchanger 20 and into separator/absorber 15 without any boost in pressure, the separator/absorber shall necessarily assume an operating pressure slightly below the operating pressure of deethanizer 17. In this case, the combined liquid stream withdrawn from the separator/absorber can be pumped to its feed position in the deethanizer. An alternative is to provide a booster blower in the vapor line to raise the operating pressure in heat exchanger 20 and separator/absorber 15 sufficiently so that the combined liquid stream can be supplied (after heat exchange with other process streams as described in Examples 1, 2 and 3) to deethanizer 17 without pumping. Still another alternative is to mount separator/absorber 15 at a sufficient elevation relative to the feed position on deethanizer 17 so that the hydrostatic head of the liquid will overcome the pressure difference.

The use and distribution of the separator liquids and the separator/absorber liquids for process heat exchange, the particular arrangement of heat exchangers for feed gas cooling, and the choice of process streams for specific heat exchange services must be evaluated for each particular application. Moreover, the use of external refrigeration to supplement the cooling available to the feed gas from other process streams may be employed, particularly in the case of an inlet gas richer than that used in Example 1.

It will also be recognized that the relative amount of feed found in each branch of the condensed liquid contained in stream 36a that is split between the two towers in FIG. 4 will depend on several factors, including gas pressure, feed gas composition and the quantity of horsepower available. The optimum split cannot generally be predicted without evaluating the particular circumstances for a specific application of the present invention. The mid-column feed positions depicted in FIGS. 4 through 6 are the preferred feed locations for the process operating conditions described. However, the relative locations of the mid-column feeds may vary depending on inlet composition or other factors such as desired recovery levels, etc. Moreover, two or more of the feed streams, or portions thereof, may be combined depending on the relative temperatures and quantities of individual streams, and the combined stream then fed to a mid-column feed position. FIGS. 4 through 6 are the preferred embodiments for the compositions and pressure conditions shown. Although individual stream expansion is depicted in particular expansion devices, alternative expansion means may be employed where appropriate. For example, conditions may warrant work expansion of the condensed liquid stream (stream 33).

The present invention provides improved recovery of $C_3$ components per amount of utility consumption required to operate the process. An improvement in utility consumption required for operating the deethanizer process may appear in the form of reduced power requirements for compression or re-compression, reduced power requirements for external refrigeration, reduced energy requirements for tower reboilers, or a combination thereof. Alternatively, if desired, increased $C_3$ component recovery can be obtained for a fixed utility consumption.

While there have been described what are believed to be preferred embodiments of the invention, those skilled in the art will recognize that other and further modifications may be made thereto, e.g. to adapt the invention to various conditions, types of feed or other requirements without departing from the spirit of the present invention as defined by the following claims.

We claim:
1. In a process for the separation of a gas stream containing methane, $C_2$ components, $C_3$ components and heavier hydrocarbon components into a volatile residue gas fraction containing a major portion of said methane and $C_2$ components and a relatively less volatile fraction containing a major portion of said $C_3$ components and heavier hydrocarbon components, in which process
   (a) said gas stream is treated in one or more heat exchange and/or expansion steps to partially condense at least a portion thereof and provide thereby at least a first vapor stream and at least one first $C_3$-containing liquid stream which also contains lighter hydrocarbons; and
   (b) at least one of said first $C_3$-containing liquid streams is directed into a distillation column wherein said liquid is separated into a second vapor stream containing predominantly methane and $C_2$ components and said relatively less volatile fraction containing the major portion of said $C_3$ components and heavier hydrocarbon components;
the improvement wherein
   (1) said second vapor stream is cooled sufficiently to condense at least a part of it, thereby forming a condensed stream;
   (2) a portion of said condensed stream is supplied to said distillation column at a top feed position;
   (3) at least a portion of said first vapor stream is intimately contacted with at least part of the remaining portion of said condensed stream in a contacting device having no more than one fractionation zone, thereby forming a third vapor stream and a second $C_3$-containing liquid stream;
   (4) said second $C_3$-containing liquid stream is supplied to said distillation column as a second feed thereto;
   (5) at least a portion of said third vapor stream is directed into heat exchange relation with said second vapor stream, thereby to supply the cooling of step (1) and thereafter discharging at least a portion of said third vapor stream as said volatile residue gas fraction;
   (6) said first $C_3$-containing liquid stream is heated and supplied to said distillation column as a third feed thereto; and
   (7) the quantities and temperatures of said feed streams to said contacting device and said distillation column are effective to maintain the overhead temperatures of said contacting device and said distillation column at temperatures whereby the major portion of said $C_3$ components and heavier hydrocarbon components is recovered in said relatively less volatile fraction.

2. The improvement according to claim 1 wherein at least a portion of said second $C_3$-containing liquid stream is heated prior to supplying said second $C_3$-containing liquid stream to said distillation column.

3. In a process for the separation of a gas stream containing methane, $C_2$ components, $C_3$ components and heavier hydrocarbon components into a volatile residue gas fraction containing a major portion of said methane and $C_2$ components and a relatively less volatile fraction containing a major portion of said $C_3$ components and heavier hydrocarbon components, in which process
   (a) said gas stream is treated in one or more heat exchange and/or expansion steps to partially condense at least a portion thereof and provide thereby at least a first vapor stream and at least one first $C_3$-containing liquid stream which also contains lighter hydrocarbons; and
   (b) at least one of said first $C_3$-containing liquid streams is directed into a distillation column wherein said liquid is separated into a second vapor stream containing predominantly methane and $C_2$ components and said relatively less volatile fraction containing the major portion of said $C_3$ components and heavier hydrocarbon components;
the improvement wherein
   (1) said second vapor stream is cooled sufficiently to partially condense it, thereby forming a partially condensed stream;

(2) said partially condensed stream is separated, thereby to form a third vapor stream and a second $C_3$-containing liquid stream;

(3) at least a portion of said second $C_3$-containing liquid stream is supplied to said distillation column at a top feed position;

(4) said third vapor stream is cooled sufficiently to condense at least a part of it, thereby forming a condensed stream;

(5) at least a portion of said first vapor stream is intimately contacted with at least a portion of said condensed stream in a contacting device, having no more than one fractionation zone thereby forming a fourth vapor stream and a third $C_3$-containing liquid stream;

(6) at least a portion of said third $C_3$-containing liquid stream is directed into heat exchange relation with said second vapor stream leaving the upper region of said distillation column, thereby to supply the cooling of step (1) and partially condense said second vapor stream;

(7) said third $C_3$-containing liquid stream is thereafter supplied to said distillation column as a second feed thereto;

(8) at least a portion of said fourth vapor stream is directed into heat exchange relation with said third vapor stream, thereby to supply the cooling of step (4) and thereafter discharging at least a portion of said fourth vapor stream as said volatile residue gas fraction;

(9) said first $C_3$-containing liquid stream is heated and supplied to said distillation column as a third feed thereto; and

(10) the quantities and temperatures of said feed streams to said contacting device and said distillation column are effective to maintain the overhead temperatures of said contacting device and said distillation column at temperatures whereby the major portion of said $C_3$ components and heavier hydrocarbon components is recovered in said relatively less volatile fraction.

4. The improvement according to claim 3 wherein at least a portion of said third $C_3$-containing liquid stream is heated prior to being directed into heat exchange relation with said second vapor stream.

5. In a process for the separation of a gas stream containing methane, $C_2$ components, $C_3$ components and heavier hydrocarbon components into a volatile residue gas fraction containing a major portion of said methane and $C_2$ components and a relatively less volatile fraction containing a major portion of said $C_3$ components and heavier hydrocarbon components, in which process (a) said gas stream is treated in one or more heat exchange and/or expansion steps to partially condense at least a portion thereof and provide thereby at least a first vapor stream and at least one first $C_3$-containing liquid stream which also contains lighter hydrocarbons; and (b) at least one of said first $C_3$-containing liquid streams is directed into a distillation column wherein said liquid is separated into a second vapor stream containing predominantly methane and $C_2$ components and said relatively less volatile fraction containing the major portion of said $C_3$ components and heavier hydrocarbon components;

the improvement wherein (1) said second vapor stream is cooled sufficiently to condense at least a part of it, thereby forming a condensed stream;

(2) at least a portion of said first vapor stream is intimately contacted with at least a portion of said condensed stream in a contacting device having no more than one fractionation zone, thereby forming a third vapor stream and a second $C_3$-containing liquid stream;

(3) at least a portion of said second $C_3$-containing liquid stream is heated and is thereafter supplied to said distillation column at a top feed position;

(4) at least a portion of said third vapor stream is directed into heat exchange relation with said second vapor stream, thereby to supply the cooling of step (1) and thereafter discharging at least a portion of said third vapor stream as said volatile residue gas fraction;

(5) said first $C_3$-containing liquid stream is heated and supplied to said distillation column as a second feed thereto; and (6) the quantities and temperatures of said feed streams to said contacting device and said distillation column are effective to maintain the overhead temperatures of said contacting device and said distillation column at temperatures whereby the major portion of said $C_3$ components and heavier hydrocarbon components is recovered in said relatively less volatile fraction.

6. In an apparatus for the separation of a gas containing methane, $C_2$ components, $C_3$ components and heavier hydrocarbon components into a volatile residue gas fraction containing a major portion of said methane and $C_2$ components and a relatively less volatile fraction containing a major portion of said $C_3$ components and heavier components, in said apparatus there being (a) one or more first heat exchange means and/or expansion means cooperatively connected to provide at least one partially condensed gas stream, (b) separation means connected to receive said partially condensed gas stream, thereby providing thereby at least a first vapor stream and at least one first $C_3$-containing liquid which also contains lighter hydrocarbons; and (c) a distillation column connected to receive at least one of said first $C_3$-containing liquid streams which is adapted to separate said stream into a second vapor stream containing predominantly methane and $C_2$ components and said relatively less volatile fraction containing the major portion of said $C_3$ components and heavier hydrocarbon components;

the improvement wherein said apparatus includes (1) second heat exchange means connected to said distillation column to receive said second vapor stream and cool it sufficiently to condense at least a part of it, thereby forming a condensed stream;

(2) dividing means connected to receive said condensed stream and to divide said condensed stream into first and second liquid streams, said dividing means being further connected to said distillation column to supply said first liquid stream to said distillation column at a top feed position;

(3) contacting and separating means connected to receive at least a portion of said second liquid stream and at least a portion of said first vapor stream wherein said liquid and vapor are commingled in a contacting device having no more than one fractionation zone, said contacting and separating means including separating means to separate the vapor and liquid after contact in said contacting device to form a third vapor stream and a second $C_3$-containing liquid stream;

(4) said contacting and separating means being further connected to said distillation column to supply said second $C_3$-containing liquid stream separated therein to said distillation column as a second feed thereto;

(5) said contacting and separating means being further connected to said second heat exchange means to direct at least a portion of said third vapor stream separated therein into heat exchange relation with said second vapor stream;

(6) first heat exchange means connected to said separation means to receive said first $C_3$-containing liquid and heat it; said first heat exchange means being further connected to said distillation column to provide said heated first $C_3$-containing liquid as a third feed thereto; and (7) control means adapted to regulate the quantities and temperatures of said feed streams to said contacting and separating means and said distillation column to maintain the overhead temperatures of said contacting and separating means and said distillation column at temperatures whereby the major portion of said $C_3$ components and heavier components is recovered in said relatively less volatile fraction.

7. The improvement according to claim 6 wherein said contacting and separating means is connected to said first heat exchange means whereby at least a portion of said second $C_3$-containing liquid stream separated therein is heated, said first heat exchange means being further connected to said distillation column to supply said heated second $C_3$-containing liquid stream to said distillation column as a second feed thereto.

8. In an apparatus for the separation of a gas containing methane, $C_2$ components, $C_3$ components and heavier hydrocarbon components into a volatile residue gas fraction containing a major portion of said methane and $C_2$ components and a relatively less volatile fraction containing a major portion of said $C_3$ components and heavier components, in said apparatus there being (a) one or more first heat exchange means and/or expansion means cooperatively connected to provide at least one partially condensed gas stream, (b) first separation means connected to receive said partially condensed gas stream, thereby providing thereby at least a first vapor stream and at least one first $C_3$-containing liquid which also contains lighter hydrocarbons; and (c) a distillation column connected to receive at least one of said first $C_3$-containing liquid streams which is adapted to separate said stream into a second vapor stream containing predominantly methane and $C_2$ components and said relatively less volatile fraction containing the major portion of said $C_3$ components and heavier hydrocarbon components;

the improvement wherein said apparatus includes (1) second heat exchange means connected to said distillation column to receive said second vapor stream and cool it sufficiently to partially condense it, thereby forming a partially condensed stream;

(2) second separating means connected to said second heat exchange means to receive said partially condensed stream and separate it, thereby to form a third vapor stream and a second $C_3$-containing liquid stream, said second separating means being further connected to said distillation column to supply at least a portion of said second $C_3$-containing liquid stream to said distillation column at a top feed position;

(3) third heat exchange means connected to said second separating means to receive said third vapor stream and cool it sufficiently to condense at least a part of it, thereby forming a condensed stream;

(4) contacting and separating means connected to receive at least a portion of said condensed stream and at least a portion of said first vapor stream wherein said liquid and vapor are commingled in a contacting device having no more than one fractionation zone, said contacting and separating means including separating means to separate the vapor and liquid after contact in said contacting device to form a fourth vapor stream and a third $C_3$-containing liquid stream;

(5) said second heat exchange means being further connected to said contacting and separating means to receive at least a portion of said third $C_3$-containing liquid stream separated therein and direct it into heat exchange relation with said second vapor stream leaving the upper region of said distillation column, thereby to cool and partially condense said second vapor stream;

(6) said second heat exchange means being further connected to said distillation column to supply said third $C_3$-containing liquid stream to said distillation column as a second feed thereto;

(7) said contacting and separating means being further connected to said third heat exchange means to direct at least a portion of said fourth vapor stream separated therein into heat exchange relation with said third vapor stream;

(8) first heat exchange means connected to said separation means to receive said first $C_3$-containing liquid and heat it; said first heat exchange means being further connected to said distillation column to provide said heated first $C_3$-containing liquid as a third feed thereto; and (9) control means adapted to regulate the quantities and temperatures of said feed streams to said contacting and separating means and said distillation column to maintain the overhead temperatures of said contacting and separating means and said distillation column at temperatures whereby the major portion of said $C_3$ components and heavier components is recovered in said relatively less volatile fraction.

9. The improvement according to claim 8 wherein said contacting and separating means is connected to said first heat exchange means whereby at least a portion of said third $C_3$-containing liquid stream separated therein is heated, said first heat exchange means being further connected to said second heat exchange means to direct said heated third $C_3$-containing liquid stream into heat exchange relation with said second vapor stream leaving the upper region of said distillation column.

10. In an apparatus for the separation of a gas containing methane, $C_2$ components, $C_3$ components and heavier hydrocarbon components into a volatile residue gas fraction containing a major portion of said methane and $C_2$ components and a relatively less volatile fraction containing a major portion of said $C_3$ components and heavier components, in said apparatus there being (a) one or more first heat exchange means and/or expansion means cooperatively connected to provide at least one partially condensed gas stream, (b) separation means connected to receive said partially condensed gas stream thereby providing thereby at least a first vapor stream and at least one first $C_3$-containing liquid which also contains lighter hydrocarbons; and (c) a distillation column connected to receive at least one of said first $C_3$-containing liquid streams which is adapted to separate said stream into a second vapor stream containing predominantly methane and $C_2$ components and said relatively less volatile fraction containing the major portion of said $C_3$ components and heavier hydrocarbon components;

the improvement wherein said apparatus includes (1) second heat exchange means connected to said distillation column to receive said second vapor stream and cool it sufficiently to condense at least a part of it, thereby forming a condensed stream;

(2) contacting and separating means connected to receive at least a portion of said condensed stream and at least a portion of said first vapor stream wherein said liquid and vapor are commingled in a contacting device having no more than one fractionation zone, said contacting and separating means including separating means to separate the vapor and liquid after contact in said contacting device to form a third vapor stream and a second $C_3$-containing liquid stream;

(3) first heat exchange means connected to said contacting and separating means to receive at least a portion of said second $C_3$-containing liquid stream separated therein and heat it, said first heat exchange means being further connected to said distillation column to supply said heated second $C_3$-containing liquid stream to said distillation column at a top feed position;

(4) said contacting and separating means being further connected to said second heat exchange means to direct at least a portion of said third vapor stream separated therein into heat exchange relation with said second vapor stream;

(5) said first exchange means further connected to said separation means to receive said first $C_3$-containing liquid and heat it; said first heat exchange means being further connected to said distillation column to provide said heated first $C_3$-containing liquid as a third feed thereto; and (6) control means adapted to regulate the quantities and temperatures of said feed streams to said contacting and separating means and said distillation column to maintain the overhead temperatures of said contacting and separating means and said distillation column at temperatures whereby the major portion of said $C_3$ components and heavier components is recovered in said relatively less volatile fraction.

* * * * *

UNITED STATES PATENT AND TRADEMARK OFFICE
CERTIFICATE OF CORRECTION

PATENT NO. : 5,771,712
DATED : June 30, 1998
INVENTOR(S) : Campbell et al.

It is certified that error appears in the above-identified patent and that said Letters Patent is hereby corrected as shown below:

Column 24, claim 10,
Line 16, "third" should read -- second --

Signed and Sealed this

Eleventh Day of December, 2001

Attest:

*Nicholas P. Godici*

NICHOLAS P. GODICI
*Attesting Officer*     *Acting Director of the United States Patent and Trademark Office*